United States Patent [19]

Weaver

[11] 4,449,536

[45] May 22, 1984

[54] METHOD AND APPARATUS FOR DIGITAL DATA COMPRESSION

[75] Inventor: Charles S. Weaver, Palo Alto, Calif.

[73] Assignee: SRI International, Menlo Park, Calif.

[21] Appl. No.: 202,457

[22] Filed: Oct. 31, 1980

[51] Int. Cl.³ ............................................. A61B 5/04
[52] U.S. Cl. .................................... 128/696; 364/417
[58] Field of Search ....................... 128/696, 711, 904; 364/415, 417, 150, 151, 178, 180

[56] References Cited

U.S. PATENT DOCUMENTS 4,098,267 7/1978 Stein et al. ........................... 128/711

OTHER PUBLICATIONS

Ruttimann et al., "IEEE Transactions on Biomedical Engineering," vol. BME-26, No. 11, Nov. 1979, pp. 613-623.
Bertrand et al., "Proceedings of the IEEE," vol. 65, No. 5, May 1977, pp. 714-721.

*Primary Examiner*—William E. Kamm

*Attorney, Agent, or Firm*—Victor R. Beckman

[57] ABSTRACT

Digital data compression method and means are disclosed which allow for transmission of digital data over a short time period and/or narrow bandwidth transmission line. Also a maximum amount of information may be stored on a movable recording medium using data compression method of this invention. Digital signals to be stored and/or transmitted first are compressed using a finite-impulse response digital compression filter which generates estimated signal values which are subtracted from actual signal values to provide a sequence of difference signals. The difference signals are encoded using a truncated Huffman type encoding method and means, and the encoded signals are transmitted to a remote receiver and/or are recorded. The receiver includes a decoder and digital reconstruction filter for exact reproduction of transmitted digital signals. The invention is well adapted for storage and/or transmission of three lead electrocardiogram (ECG) signals, recording and playback of music, and the like.

26 Claims, 11 Drawing Figures

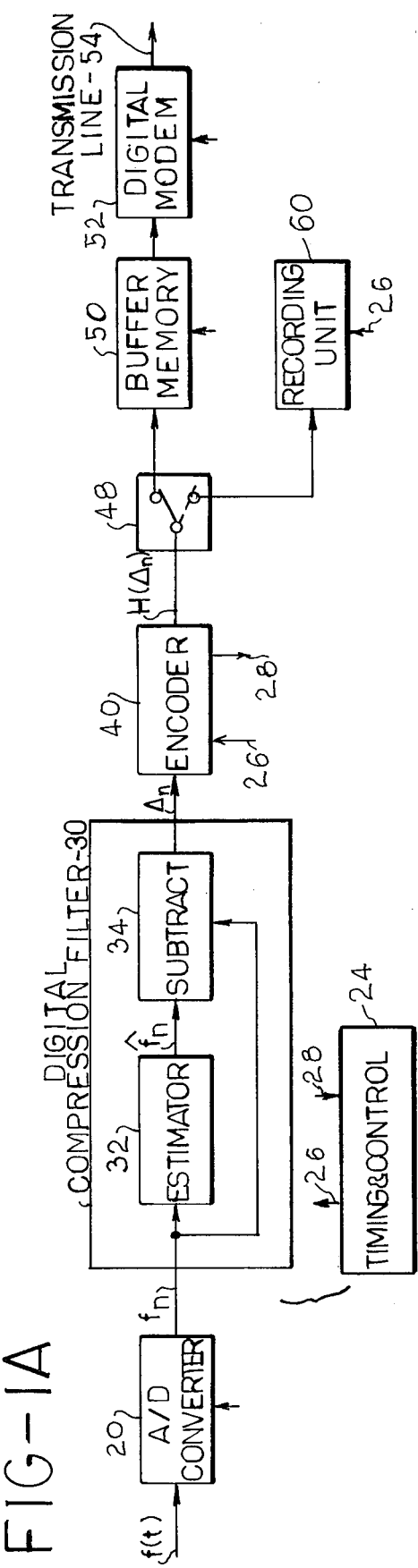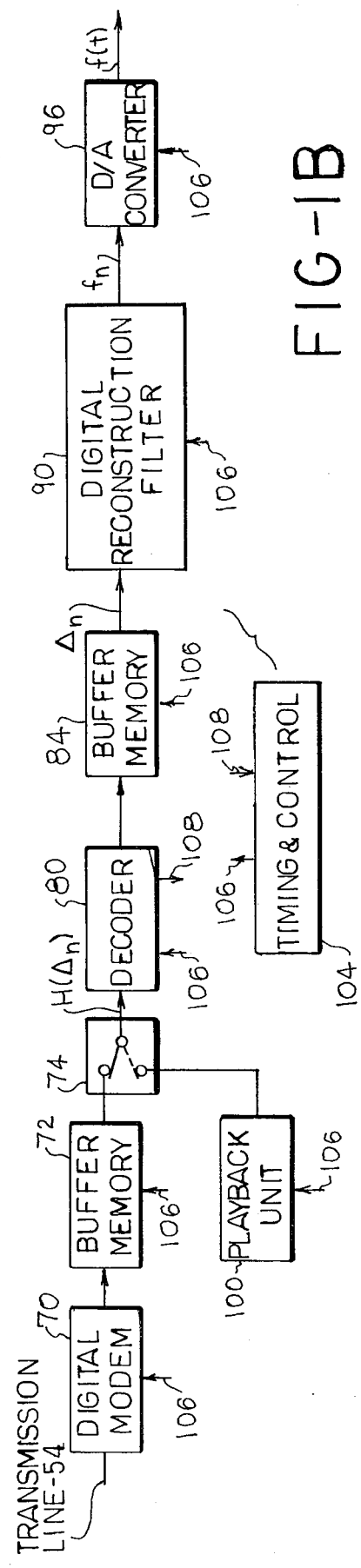

| $\Delta_n$ | CODE | ROM250 OUTPUT | APPROXIMATE PROBABILITY | WORD LENGTH | TREE |
|---|---|---|---|---|---|
| -3 | 00000001 | 10000000 | 0.011 | 8 | |
| 3 | 0000001 | 01000000 | 0.012 | 7 | |
| else(-4) | 000001 | 00100000 | 0.018 | 6 | |
| -2 | 00001 | 00010000 | 0.057 | 5 | |
| 2 | 0001 | 00001000 | 0.059 | 4 | |
| -1 | 001 | 00000100 | 0.189 | 3 | |
| 1 | 01 | 00000010 | 0.188 | 2 | |
| 0 | 1 | 00000001 | 0.467 | 1 | |

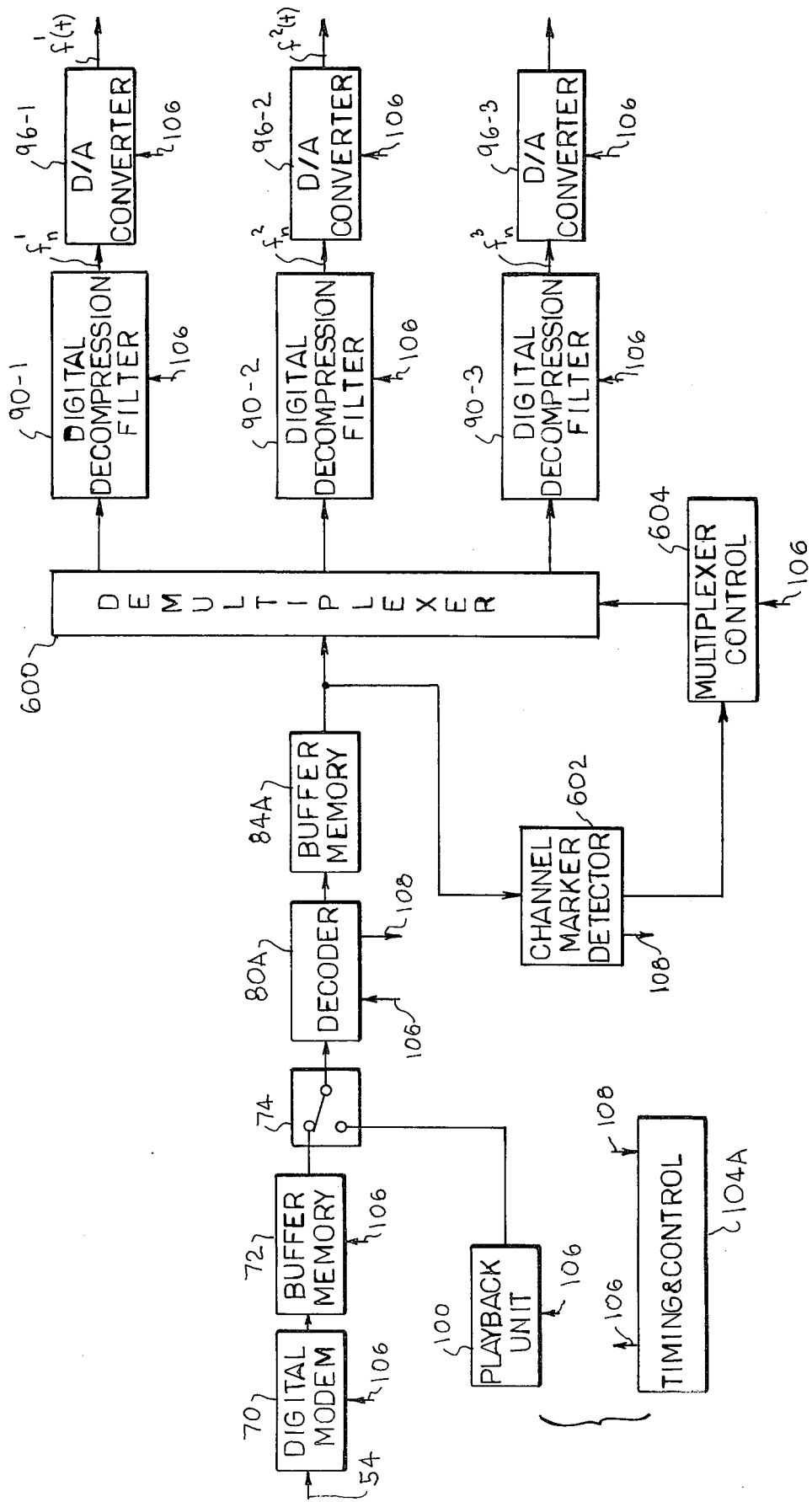

METHOD AND APPARATUS FOR DIGITAL DATA COMPRESSION

BACKGROUND OF THE INVENTION

Physiological data, such as electrocardiographic (ECG) data, often is transmitted to a centralized location for processing and analysis. Such transmitted data, for example, may be supplied directly to a computer for computer analysis thereof. For real-time analysis, telephone transmission of the ECG waveforms from the doctor's office to the computer provides the necessary speed of transmission. Presently, the most commonly used method of transmitting ECG waveforms by telephone transmission is by use of FM subcarriers. (See, for example, U.S. Pat. No. 3,199,508). If these systems are well designed and properly maintained, waveforms of reasonable quality can be transmitted. However, those units installed in doctors' offices or in hospitals frequently do not receive the necessary servicing required for proper operation thereof. This shortcoming has resulted in a search for methods of transmitting the data digitally by first converting the analog ECG waveforms into digital form.

It is highly desirable that a vector ECG (i.e. three channels of ECG) be transmitted for analysis. However, the bandwidth of conventional telephone transmission circuits is not sufficiently wide to accommodate a vector ECG without data reduction. With the present invention, the average bit rate of an analog-to-digital-converted vector ECG is reduced sufficiently to allow for digital transmission thereof over a low-grade dial-up telephone line. A method of reducing the average bit rate of digitized ECG signals by use of a second-order digital compression filter followed by a Huffman-type encoder is disclosed in an article by U. E. Ruttiman and H. V. Pipberger entitled "Compression of the ECG by Prediction or Interpolation and Entropy Encoding", *IEEE Transactions on Biomedical Engineering*, Vol. BME-26, No. 11, pp. 613–623, Nov. 1979. Also, the recording of encoded digitized ECG signals is disclosed in an article by K. L. Ripley and J. R. Cox, Jr. entitled, "A Computer System for Capturing Transient Electrocardiographic Data", *Proc. Comput. Cardiol.* pp. 439–445, 1976. There, digitized ECG signals are second-differenced using computer software, the second-differenced values are Huffman encoded, again using computer software, and the serial bit stream is stored on disc storage means.

SUMMARY OF THE INVENTION

The invention involves a data collection system wherein three analog ECG signals are processed using three input signal channels, each of which channels includes an analog-to-digital converter for converting the analog signals to digital fixed length sample signals. Digital compression filters in the channels generate digital difference signals related to the difference between the sample signal and an estimated value thereof. A multiplexer connects the three digitized and compressed ECG signals to an encoder for encoding the same. The encoded signal may be transmitted over standard telephone transmission lines to a remote receiver. A decoder at the receiver decodes the signals, and a demultiplexer sequentially connects the decoded output to three receiver channels, each of which channels includes a digital decompression filter from which filters the fixed length sample signals are recovered. If desired, the digital ECG signals may be converted to analog form by use of three digital-to-analog converters responsive to the three decoder outputs. A stable compression-decompression filter combination is disclosed which does not require reinitialization after transmission bit stream errors.

BRIEF DESCRIPTION OF THE DRAWINGS

The invention will be better understood from the following description when considered with the accompanying drawings. In the drawings, wherein like reference characters refer to the same parts in the several views:

FIGS. 1A and 1B together show a block diagram of a digital transmission and receiving system which embodies the present invention, there being shown a digital transmitter unit in FIG. 1A and receiver unit in FIG. 1B;

FIGS. 8A and 8B together show a block diagram of a digital transmission system for digital transmission of three lead electrocardiograph signals over standard telephone transmission lines.

Figure 2:
FIG. 2 shows a waveform and graphic representations of signals appearing at various locations in the system shown in FIGS. 1A and 1B.

Reference first is made to FIG. 1A wherein the transmitting unit of the system is shown comprising an analog to digital converter (A/D converter) 20 for conversion of an analog input signal f(t) into digital form, the $n^{th}$ sample from the analog to digital converter 20 being identified as $f_n$. At A of FIG. 2, an analog signal 22 is shown which comprises an input to the analog to digital converter 20. The form of the analog to digital converter output is shown at B of FIG. 2. There the A/D converter output is shown comprising samples $f_{n-1}$ through $f_{n+i}$ of equal length words. The analog to digital converter 20 operates at a sampling rate established by control signals from a timing and control unit 24 supplied thereto over transmitter timing line 26. As employed herein, line 26 from the timing and control unit 24 represents a plurality of timing circuit outputs, one or more of which are supplied to the system elements for proper system timing and control. Inputs also are supplied to the timing and control unit over line 28 for control thereof by signals from various other system elements in a manner described in detail hereinbelow. For present purposes, it will be understood that the A/D converter 20 operates in a conventional manner at a fixed sampling rate and with a fixed word length output.

The digital output from the A/D converter 20 is supplied to a digital compression filter 30 which, for purposes of description only, is shown to include an estimator 32 and subtracting means 34. The estimator 32 provides an estimate of $f_n$, here identified as $\hat{f}_n$, based upon actual samples occuring both before and after the sample $f_n$ to be estimated. Estimators for providing such estimated $\hat{f}_n$ values are, of course, well known. A difference signal $\Delta_n$ is produced by the compression filter 30 comprising the difference between the actual signal input $f_n$ and the estimated signal value $\hat{f}_n$ by subtraction of the estimated value from the actual value at subtracting means 34, as follows:

$$\Delta_n = f_n - \hat{f}_n \quad (1)$$

In the graphic signal representation of the compression filter output, shown at C in FIG. 2, difference signals $\Delta_n, \Delta_{n+1}, \Delta_{n+2}, \Delta_{n+3}, \Delta_{n+4} \ldots \Delta_{n+i}$ are shown, with actual difference signal values being shown in parenthesis beneath the symbols for purposes of illustration only.

The difference signal values $\Delta_n$ are supplied to an encoder 40 employing a truncated Huffman code for encoding the same. Huffman encoding is disclosed in an article by D. A. Huffman entitled, "A Method for the Construction of Minimum Redundancy Codes", Proceedings of the IRE, Vol. 40, page 1098, September 1952. Truncated Huffman encoding also is known as disclosed, for example, in the articles mentioned in the Background of the Invention, above. In brief, the Huffman encoding technique makes use of the fact that the compression filter 30 has difference signal outputs, $\Delta_n$, having different probabilities of occurance, and uses this fact to achieve a reduction in the total number of bits in the encoded signal over the input signal. A single code word is assigned to infrequently occuring difference signals, and supplied as a label for the actual difference signal value $\Delta_n$. In FIG. 1A, the encoder 40 output is designated $H(\Delta_n)$ and, at D in FIG. 2, the values $H(\Delta_n)$, $H(\Delta_{n+1})$ etc. represent encoded values of $\Delta_n, \Delta_{n+1}$, etc. The most frequently occuring value of $\Delta_n$ (here zero) is encoded using the shortest code word. A truncated Huffman code is disclosed hereinbelow which is readily implemented using a simple encoder and decoder, also described in detail below. For present purposes, it will be understood that the encoder 40 output comprises code words for the most frequently occuring values of $\Delta_n$, together with a combined code word label and actual value of the difference signal $\Delta_n$ for less frequently occuring values of $\Delta_n$. For purposes of illustration, if the difference signal value exceeds $\pm 3$ then the actual difference signal $\Delta_n$ together with a code word label is produced at the encoder output. At D of FIG. 2, wherein the encoded difference values are shown, it will be seen that the encoded value for $\Delta_{n+2}$ comprises a label and the actual difference signal $\Delta_{n+2}$ for the infrequently occuring difference value of $\Delta_{n+2}$, here six (6).

The encoded signals from encoder 40 are transmitted to a remote receiver and/or are recorded. For transmission to a remote receiver, the encoder output is connected through a switch 48 to a buffer memory 50 and thence through a digital modem 52 for transmission over transmission line 54. With the switch 48 in the other, broken line, position, the encoder output is supplied to a recording unit 60 for recording of the encoded difference signals and labeled $\Delta_n$ signals.

When telephone transmission is employed, for example, the encoded signals are transmitted over line 54 to a digital modem 70 at the receiver shown in FIG. 1B. The modem output is buffered by buffer memory 72, and the buffer memory output is supplied through a switch 74 to a decoder 80 for decoding the truncated Huffman encoded signals. At the decoder 80, the Huffman code words are converted to the original difference signals $\Delta_n$. Where the Huffman code word comprises a labeled actual difference signal, the label is stripped therefrom, and the actual difference signal without the label is supplied to the decoder output. Encoding and decoding means which may be used in the present invention are described in greater detail hereinbelow.

The difference signals $\Delta_n$ from the decoder 80 are supplied to a reconstruction, or decompression, filter 90, through a small, one word, buffer memory 84. As will become apparent, the decoder output signals are produced at varying rates, and the small buffer memory 84 is included to accommodate the input rate requirements of the reconstruction filter 90. From the difference signal values, actual signal values $f_n$ for every sample are determined at the reconstruction filter 90. A novel compression filter reconstruction filter combination is disclosed in detail hereinbelow, which combination is stable whereby transients in the decoder output produced by bit stream errors essentially disappear after a small number of error-free signals are transmitted, without the need for elaborate bit recovery schemes. A digital to analog converter (D/A converter) 96 converts the actual signal samples $f_n$ from the digital reconstruction filter 90 to analog form, and any desired use may be made of the analog signals. A receiver timing and control unit 104 supplies timing signals to the various receiver elements over line 106 for proper timing of the receiving operation. Also, control signals for the unit 104 are supplied thereto over line 108 from various elements of the receiver for control thereof in a manner described in greater detail hereinbelow.

Recorded encoded digital signals, such as those recorded at recording unit 60, FIG. 1A, may be supplied to the decoder 80 for decoding and subsequent processing. With switch 74 in the broken line position, signals are supplied to the decoder 80 from a playback unit 100.

As noted above in the description of FIG. 1A, the digital compression filter 30 includes an estimator 32 having an output comprising an estimated sample value $\hat{f}_n$ based upon actual samples $f_{n-1}$ and $f_{n+1}$ occuring before and after the sample $f_n$ to be estimated. Often prior art estimators are used which provide an output.

$$\hat{f}_n = a_1 f_{n+1} + a_2 f_{n-1} \quad (2)$$

where the coefficients $a_1$ and $a_2$ are chosen to minimize the mean square error of the difference $\Delta_n$, where $\Delta_n = f_n - \hat{f}_n$, as noted in equation (1), above. For compression of ECG signals, for example, the coefficients $a_1$ and $a_2$ are substantially optimum when they equal 0.5. Consequently, for $a_1 = a_2 = 0.5$, equations (1) and (2) may be combined to give $$\Delta_n = 0.5 [f_{n+1} - 2f_n + f_{n-1}] \quad (3)$$
$$= 0.5 f_{n+1} - f_n + 0.5 f_{n-1}$$

It will be seen that the quantity inside the brackets is the second difference of $f_n$ and, since the sample rate is greater than the Nyquist rate, the second difference is equivalent to the second derivative. Digital data compression systems which employ such a double difference compression filter include a reconstruction filter of the double integration type in the receiver unit for decoding such double difference signals. Thus, where a prior art double difference type compression filter 30 is employed in the system, an associated double integration type reconstruction filter 90 would be employed therewith. In such a case, the reconstruction filter 90 would operate to make use of the following equations:

$$f_{n+1} = \frac{\hat{f}_n}{a_1} - \frac{a_2}{a_1} f_{n-1} \quad (4)$$

$$= \frac{f_n - \Delta_n}{a_1} - \frac{a_2}{a_1} f_{n-1} \quad (5)$$

From equation (5), which is recursive, it will be apparent that two adjacent sample values together with the value of $\Delta_n$ are required for the solution thereof. Thereafter, only the values of $\Delta_n$ are required. Similar algorithms can be derived for any number of coefficients.

The above described prior art double difference-double integration filter combination is unstable such that bit errors in the transmission of data between the compression and reconstruction filters result in a random ramp from the reconstruction filter which is added to signals following the bit error. Error-free transmission, or the use of error recovery means, is required for proper operation of such a compression-reconstruction filter combination. (A modified compression-reconstruction filter combination which is stable, and which may be employed in the present invention, is described below.)

Figures 3, 4:
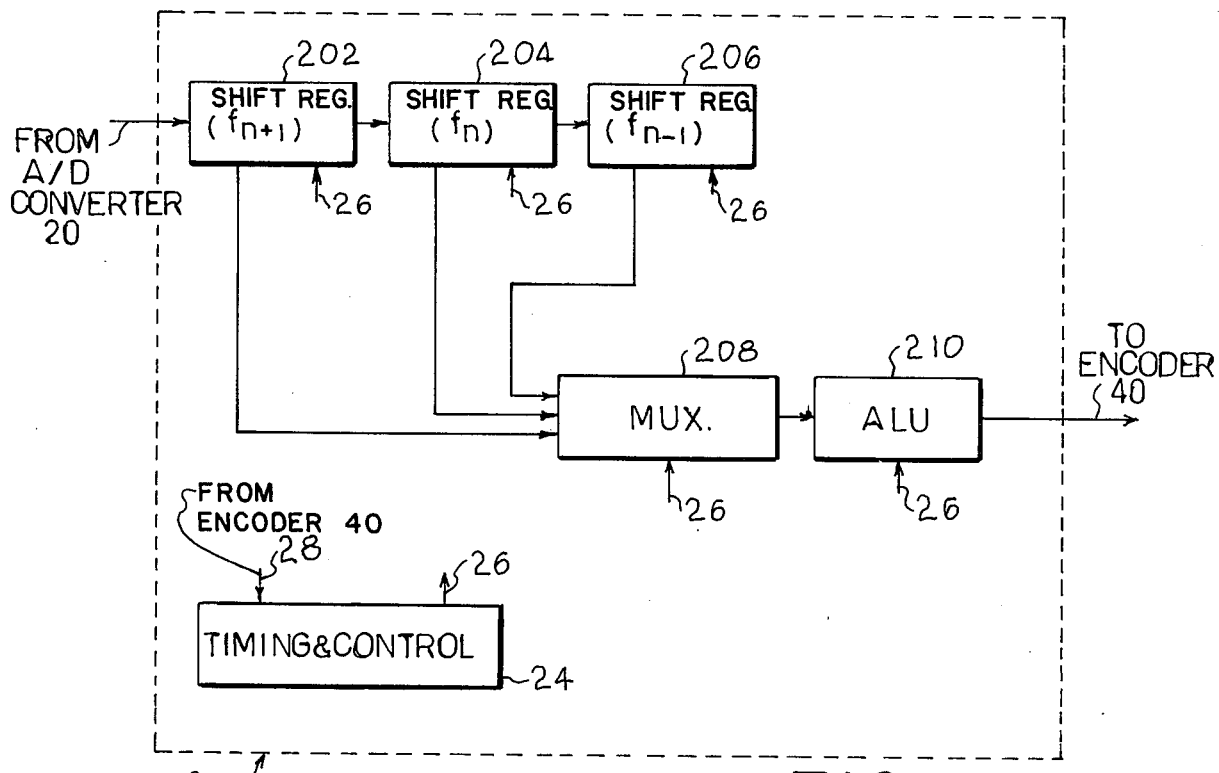
FIG. 3 is a table showing a truncated Huffman code for use with the present system.
FIG. 4 is a block diagram showing details of a novel compression filter of the type which may be used in the unit shown in FIG. 1A.

A truncated Huffman code which may be used in the illustrated system is shown in the table of FIG. 3. The difference signals, $\Delta_n$, which occur most frequently are assigned a code word. Where the input to the system comprises a digitized ECG signal, and a digital compression filter of the above-described type is employed, the probability of $\Delta_n$ comprising a value of between +3 and −3 is, approximately, 0.98. These difference signals are assigned different length code words, with the most frequently occuring difference signal being assigned the shortest code word. All other difference signals outside the range of ±3 are identified as else in the table, and these are assigned a code word which, as described above with reference to FIG. 2, comprises a label for the actual difference value $\Delta_n$ which subsequently is recorded and/or transmitted. With the present system, the transmission of the actual $\Delta_n$ value contributes approximately 0.16 bits to the average per symbol (about 10%). However, this is not 10% added to the untruncated Huffman code bit rate, because the code words in the latter code that are assigned to the $\Delta_n$'s that make up else in the truncated code will be no longer than the word that indicates that else has occured in the truncated code.

In FIG. 3, the approximate probability of occurance of the difference signals $\Delta_n$ is shown to range from 0.467 maximum to 0.011 minimum. The unique code word set comprises a 1's bit in the least significant bit position. Any other bit position comprises a zero bit. As will become apparent, simple coding and decoding hardware may be used in implementing the code. The decoder can be represented by the tree included in FIG. 3, where the left branches represent 0's and right branches 1's. The final branches, which are all 1's in this case, indicate the decoded word. The starting bit is entered at the bottom of the tree and the branches are followed until a final branch is reached, then the tree is reentered at the bottom.

Reference now is made to FIG. 4 wherein a digital compression filter 30 is shown of the type which may be included in the transmitting and/or recording section of the system illustrated in FIG. 1A. The compression filter includes a series of shift registers 202, 204, and 206 into which consecutive sample signals from the A/D converter 20 are shifted. In FIG. 4, for purposes of description, the registers 202, 204 and 206 are shown to contain samples $f_{n+1}$, $f_n$ and $f_{n-1}$, respectively. For 8-bit samples, 8-bit registers are employed. The register outputs are connected to a digital multiplexer 208 for selective connection of the sample signals to an arithmetic and logic unit (ALU) 210. Both the multiplexer 208 and the ALU 210 are under control of the timing and control unit 24.

Equation (3) may be utilized by the illustrated compression filter in the generation of the difference signal $\Delta_n$. An estimate $\hat{f}_n$ of the sample $f_n$ is made using the samples either side of $f_n$, i.e. $f_{n-1}$ and $f_{n+1}$, but not $f_n$ itself. Multiplying of the samples by 0.5 simply involves shifting of the bits toward the least significant bit. Under control of unit 24, the words $f_{n-1}$ and $f_{n+1}$ are moved into the ALU 210 through the multiplexer 208 and added. The sum is shifted one bit to the right for the required division to provide the estimated value $\hat{f}_n$. The actual sample $f_n$ then is moved into the ALU 210 through the multiplexer 208 and subtracted from $\hat{f}_n$ to provide the difference signal value $\Delta_n$ at the ALU 210 output, which then is supplied to encoder 40 (FIG. 1A). The arithmetic in the ALU 210 is done in a word length that is at least one bit longer than the sample word length from the A/D converter 20 to ensure against round-off-error.

In the generation of $\Delta_n$, it will be noted that all necessary multiplication is done by shifting, which, of course, may be done at a high speed. No multiplier is required for performing the necessary multiplication. Multipliers operate at such a slow rate that use thereof in the present system would, essentially, render the system useless for its intended purpose; i.e. that of transmitting and/or storing large amounts of information in a short period of time using narrow band transmission lines and/or minimum storage space. It here will be noted that equation (3) simply is illustrative of a general type of equation which may be used in the operation of the digital data compression filter and this aspect of the invention is discussed in greater detail hereinbelow.

Figure 5:
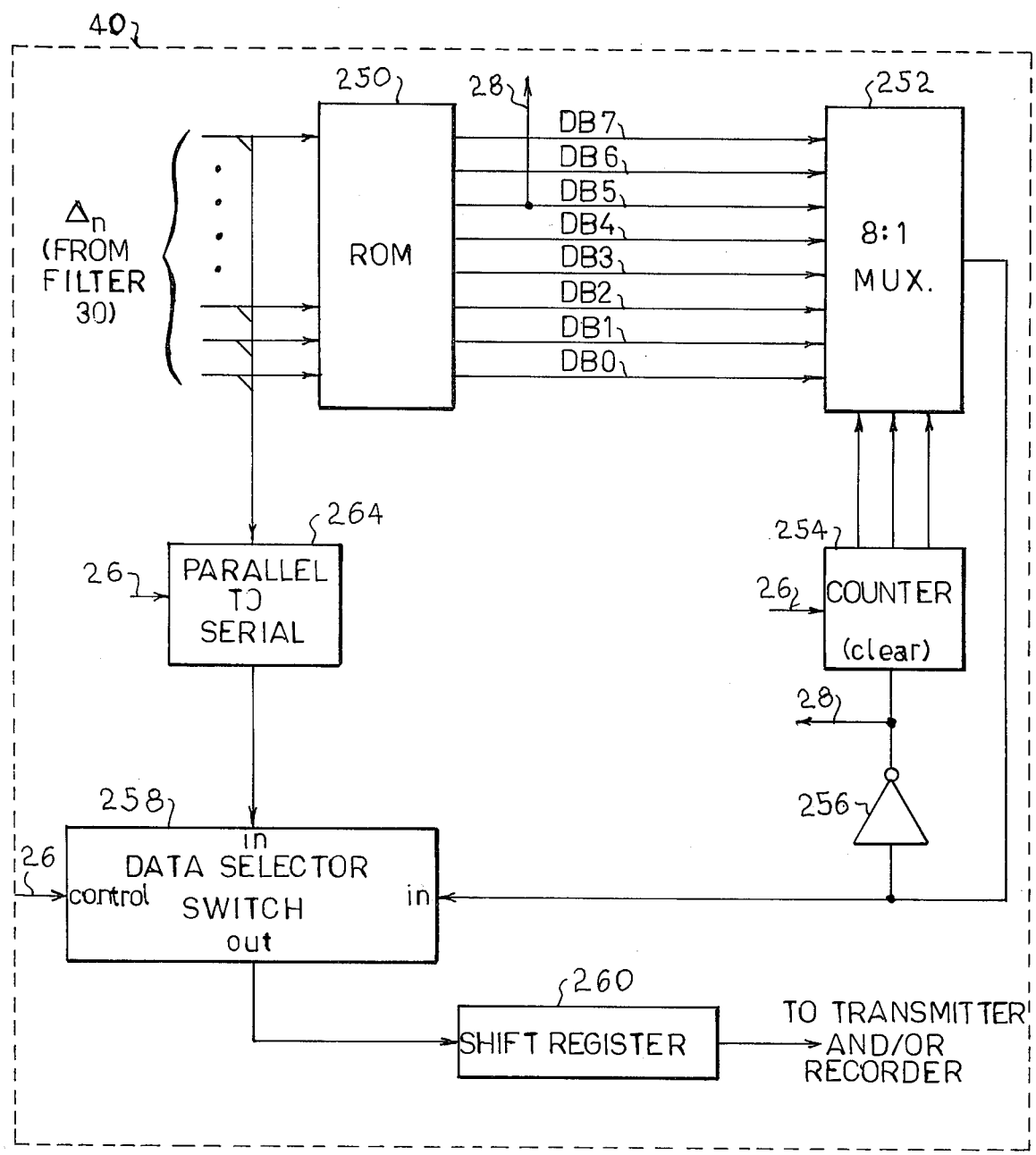
FIG. 5 is a block diagram showing details of a truncated Huffman encoder of the type which may be used in the unit shown in FIG. 1A.

The encoder 40, to which the difference signal $\Delta_n$ is supplied from the digital compression filter 30 is shown in FIG. 5. There, the encoder is shown comprising a read only memory, ROM, 250 to which the difference signal, $\Delta_n$, from the ALU 210 of FIG. 4 is supplied as an address input. The ROM stores the following 8 bit words:

00000001
00000010
00000100
00001000
00010000
00100000
01000000
10000000

These outputs also are included in the table shown in FIG. 3 adjacent the difference signal $\Delta_n$ input which produces the same. For example, an input of 2 addresses the location where 00001000 is stored. Any $\Delta_n$ input in the else catagory, here, outside the range of ±3 will address a location where 00100000 is stored.

The ROM outputs are supplied as inputs to an 8:1 multiplexer 252 which is addressed by the output from a counter 254. The counter is driven by clock pulses from timing and control unit 24 (FIG. 4) and is cleared by application of a signal supplied thereto from the multiplexer output through an inverter 256. In the above example, wherein a $\Delta_n$ signal of 2 provides an output of 00001000 from the ROM, data line DB3 is high and the others are low. Bits are serially switched from the ROM 250 by operation of the multiplexer 252, until the first 1 output is reached, at data line DB3 in this example, at which time a clear signal is supplied to the counter 254 through inverter 256 to clear the same. Another output from the inverter 256 to the timing and control unit 24 stops the clock input to the counter until the next $\Delta_n$ signal to the encoder. The multiplexer output also is connected through a switch 258 to a shift register 260 whereby the ROM 250 output is serially switched into the shift register 260 until the first 1 appears. In the present example, the shift register 260 is loaded with the code word 0001, using the shift-left serial input of the register. Essentially, this multiplexer operation serves to strip the ROM output of bits at higher bit positions than the first 1. Code words entered into the register 260 are shifted out therefrom for transmission and/or recording.

As noted above, any difference signal $\Delta_n$ in the else catagory, here outside the range of ±3, addresses a location where 00100000 is stored, wherein data line DB5 is high and the others are low. Line DB5 is connected to the timing and control unit 24 (FIG. 4) through line 28. With this input to the control unit 24, the switch 258 is operated for connection of the input of the shift register 260 to the data compression filter output through a parallel to serial conversion register 264. Now, the actual difference signal $\Delta_n$ is entered into the register 260, again using the shift left serial input of the register. As mentioned above, the code word for else serves as a label for the actual difference signal $\Delta_n$ to identify the same for decoding.

Figure 6:
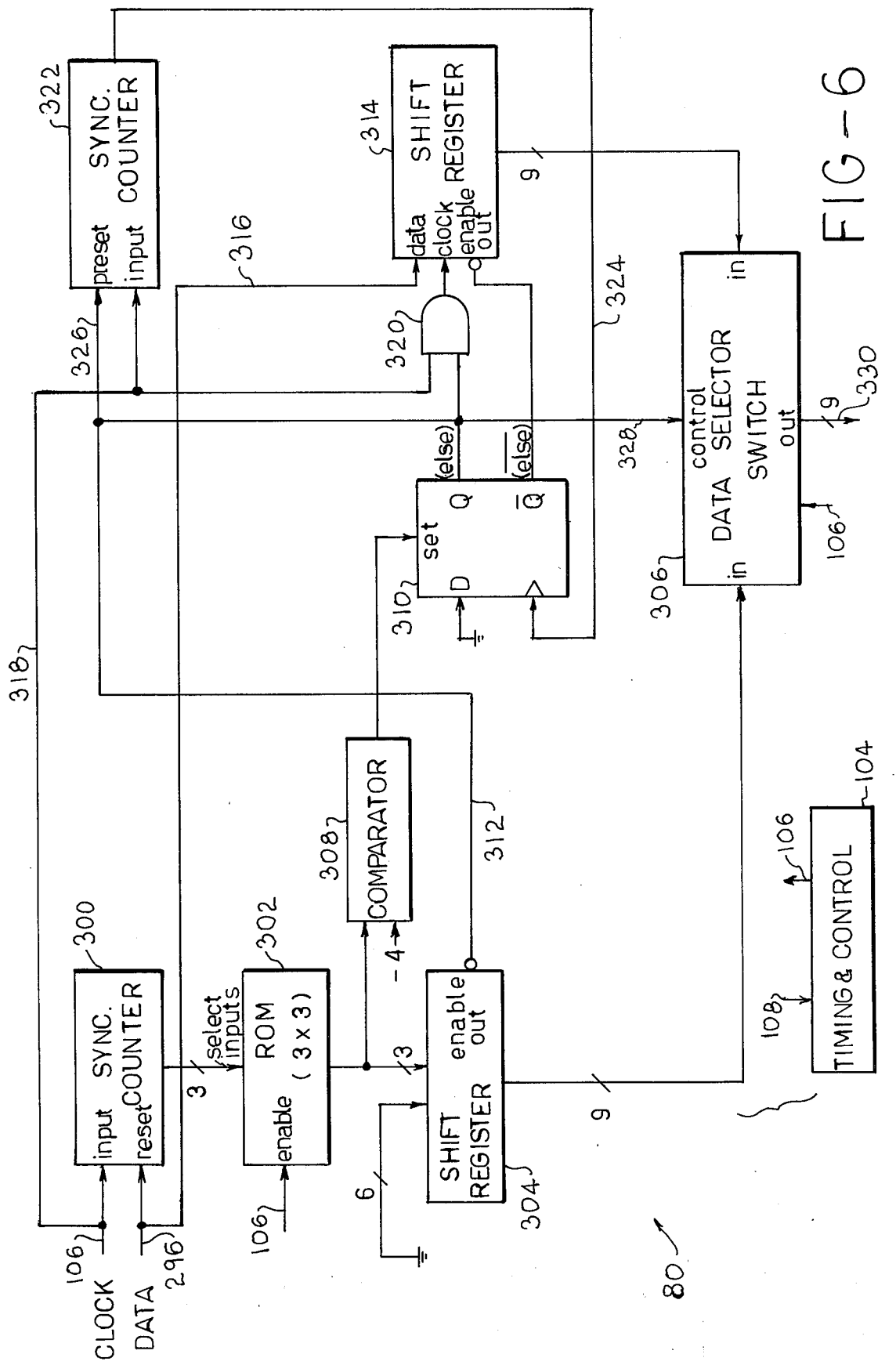
FIG. 6 is a block diagram showing details of a decoder of the type which may be used in the unit shown in FIG. 1B.

After transmission or playback the coded difference signals, $H(\Delta_n)$, are converted to actual difference signal values $\Delta_n$ by the decoder 80, shown in detail in FIG. 6. There, the data stream at line 296 (depicted at D of FIG. 2) is supplied as a reset signal to a synchronous counter 300. Clock pulses at line 106 from timing and control unit 104 are supplied to the counter input to clock the same; the data stream and clock operating at the same rate. Counting proceeds so long as the data input is LOW. When the input data line 296 goes HIGH, the counter 300 is reset.

The output from the counter 300 is supplied to a read only memory (ROM) 302, to address the same. The ROM 302 serves as a code converter for decoding the Huffman encoded difference signals, $H(\Delta_n)$ here represented by the number of zeros counted by the counter 300 prior to being reset by a one in the data stream. With the illustrated code shown in FIG. 3, the ROM 302 generates the difference signal values −3, −2, −1, 0, 1, 2 and 3, dependent upon the number of zeros between ones counted by the counter 300. The number −4 is generated when the "else" symbol is present in the data stream, i.e. when five (5) zeros between ones are counted. It will be apparent that three bits are required to represent the eight different counts from the counter 300 and the eight decoded values from the ROM 302.

The ROM 302 is enabled immediately prior to resetting of the counter 300 by application of an enable signal supplied thereto from the timing and control unit 104 over line 106. When enabled, the three bit output is supplied to the three least significant bit inputs of a shift register 304. Arithmetic performed in the digital reconstruction filter 90 (shown in FIG. 1A and in detail in FIG. 7) is done in 9 bits to prevent round-off error. Therefore, six leading zeros are added to the three bit ROM 302 output to form the 9 bit input for the digital filter. The shift register 304 supplies the necessary zeros by connecting the six most significant bit inputs to a source of zeros, here ground. The 9 bit register output is supplied to one input of a data selector switch 306. Unless the number −4 is generated by the ROM 302, the output from the register 304 is connected through the data switch 306 to the buffer amplifier 84 (FIG. 1B) and thence to the digital reconstruction filter 90.

It will be seen that the ROM output also is supplied to a digital comparator 308. The decoded label "else", here, −4, is supplied as a second input to the comparator. When the ROM output is −4, the comparator output goes HIGH and sets a flip-flop 310 whereupon the Q (else) output from the flip-flop goes HIGH. The HIGH signal from the flip-flop is connected to the enable terminal of the register 304 over line 312 to disable the output from the register. As a result, the decoded label does not appear at the output from the register 304. Instead, the actual value of $\Delta_n$ at data input line 296 is shifted into a shift register 314 over line 316.

Clock pulses for the shift register 314 are supplied thereto over line 318 from clock input line 106 through an AND gate 320, which gate is enabled by the HIGH Q output from flip-flop 310. The number of bits shifted into register 314 is determined, of course, by the number of clock pulses supplied thereto through the AND gate. The flip-flop is reset to disable the gate 320 when the actual difference signal, $\Delta_n$, has been shifted into the register 314. In the illustrated arrangement the flip-flop is reset by application of a signal to the clock input thereof from a synchronous counter 322 over line 324. The counter 322 is of the programmable type, and is set to the value 9 upon receipt of a HIGH from the Q output of flip-flop 310 at the preset input thereof over line 326. Clock pulses at the counter input now cause the counter to count down from 9 to zero. When the counter output goes to zero, the flip-flop 310 is reset upon application of a LOW to the D input thereof at the time of the clock pulse input. In this manner, 9 data bits are shifted into the register 314. The register 314 is a tri-state device, the output from which is enabled by application of a LOW to the Enable Out terminal thereof from the flip-flop 310. The HIGH from the Q output of the flip-flop 310 is supplied to the data selector switch 306 over line 328 to control the switch for passage of the shift register 314 output to the outlet lines 330 of the switch. As seen in FIG. 1B and described above, the output from the decoder 80, shown in detail in FIG. 6, is supplied to the digital reconstruction filter 90, shown in detail in FIG. 7, through the buffer memory 84.

Figure 7:
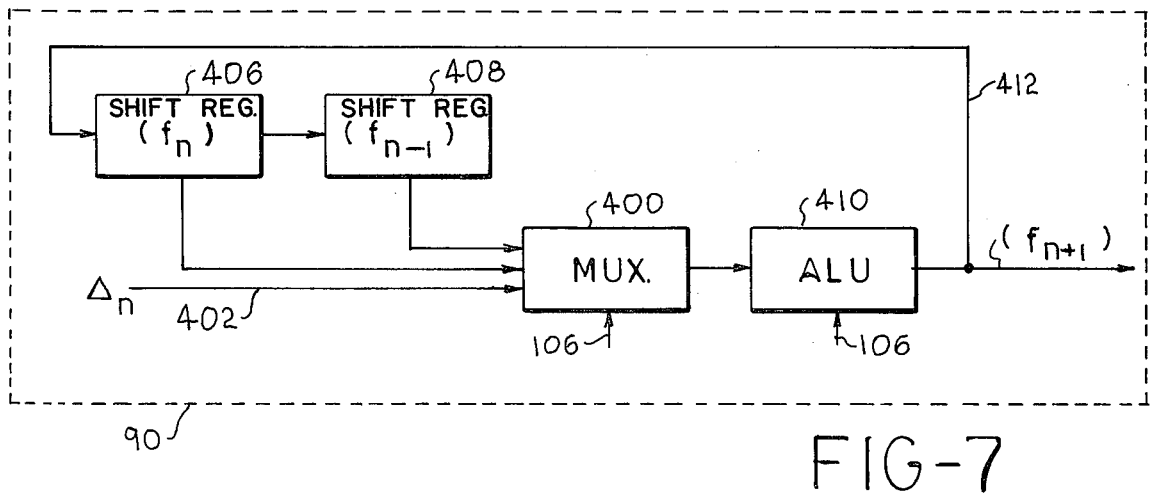
FIG. 7 is a block diagram showing details of a novel reconstruction filter of the type which may be used in the unit shown in FIG. 1B.

A digital reconstruction filter 90 for implementing equation (5) is shown in FIG. 7, to which figure reference now is made. As noted above, this equation is recursive, requiring two adjacent actual signal values together with an associated difference signal value $\Delta_n$ for solution, after which only the values of $\Delta_n$ are required. The illustrated reconstruction filter 90 comprises a 3 to 1 digital multiplexer 400 having one input 402 to which difference signals $\Delta_n$ from the decoder 80 are supplied through buffer memory 84. Two other inputs to the multiplexer 400 are provided by series connected shift registers 406 and 408, which registers contain the values $f_n$ and $f_{n-1}$, respectively. The $\Delta_n$, $f_n$ and $f_{n-1}$ values at the input to the multiplexer 400 are supplied through the multiplexer to an arithmetic and logic unit (ALU) 410 where the required multiplication by shifting, addition, and subtraction for the solution of equation (5) take place, all under control of timing and control unit 104 shown in FIG. 7. The output from the reconstruction filter, comprising the value of $f_{n+1}$ calculated by the ALU 410, is supplied to the digital to analog converter 96 (FIG. 1B) for conversion to analog form. The calculated $f_{n+1}$ value is shifted into register 406 over line 412 while the value of $f_n$ contained in the register 406 simultaneously is shifted into register 408. Now, with the next value of $\Delta_n$ at line 402, the above-described process is repeated for calculation of the next actual signal value. As noted above, in the implementation of equation (5) the arithmetic in the ALU is done in 9 bits to prevent round off error.

Implementation of equation (5) by the reconstruction filter 90 requires loading of the registers 406 and 408 with actual sample signals before calculation of values for $f_{n+1}$ are possible. The compression-decompression filter combination which includes filter 90 is unstable and requires reinitialization following bit errors. Under conditions wherein bit errors substantially never occur, as for example in the recording and playback of signals, without transmission thereof, operation using the compression filter 30, reconstruction filter 90 combination implementing equations (3) and (5) is satisfactory. A modified compression-reconstruction filter combination which is stable is described hereinbelow following description of a system for transmitting three ECG signals.

Figure 8A:
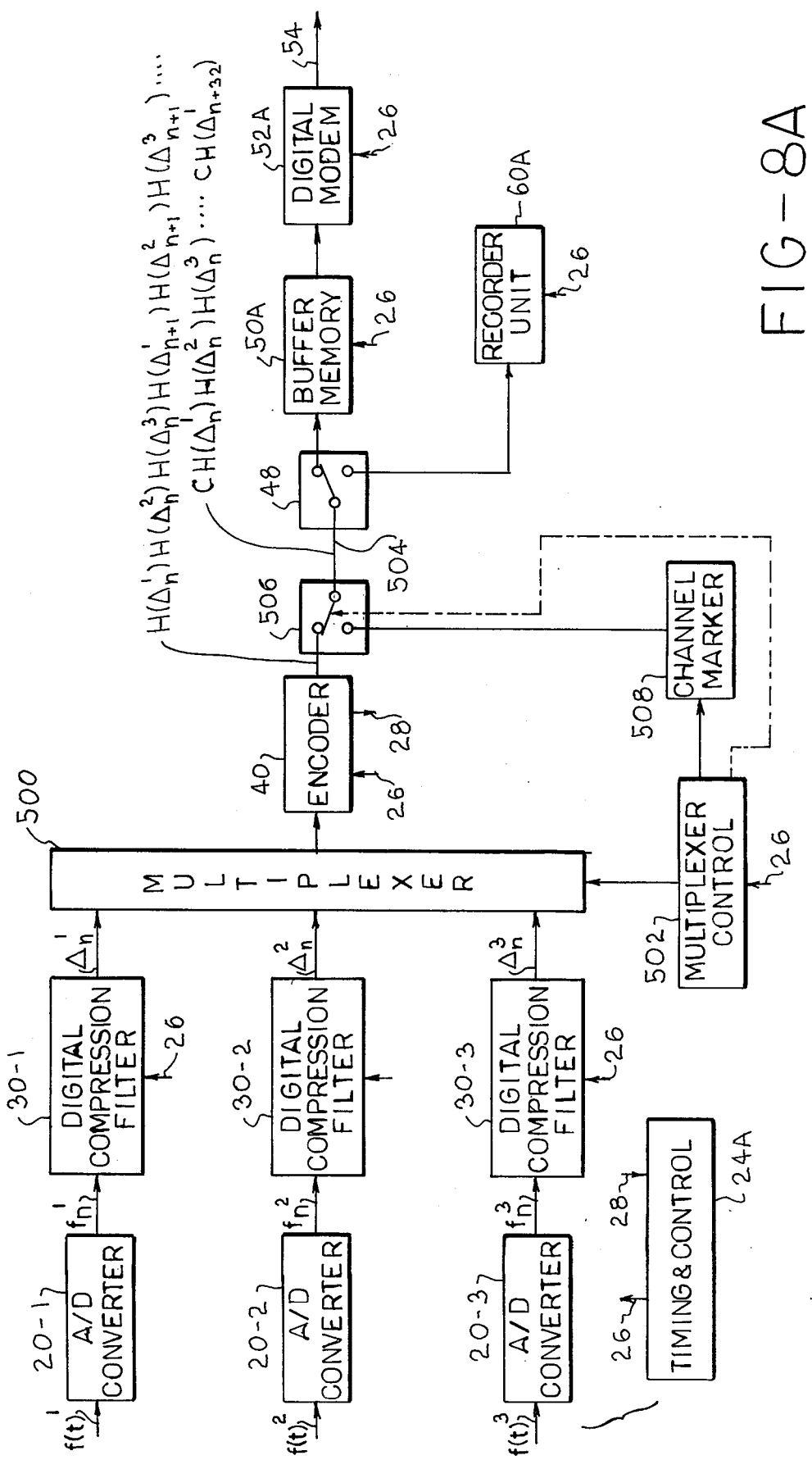

There is a wide variety of applications for the data compression method and apparatus of the present invention, including use thereof for transmission of ECG signals from doctors' offices and hospitals to computer centers for automatic analysis and storage. ECG computer analysis requires an ECG fidelity that is most practically obtained by digital transmission. However, standard telephone lines are not of sufficient bandwidth to permit 3-lead transmission in a digital mode, without data compression. By use of the present invention, simultaneous transmission of three ECG leads over an ordinary telephone line is possible. Transmitting and receiving units for 3-lead ECG transmission over ordinary telephone lines are shown in FIGS. 8A and 8B, respectively. In FIG. 8A, three ECG analog signals are shown supplied to individual analog to digital A/D converters 20-1, 20-2 and 20-3, which converters have, for example, 8 bit outputs and operate at a sample rate of 250 bits/sec. The digitized outputs from the A/D converters are supplied to digital compression filters 30-1, 30-2 and 30-3, which may be of the same type as digital compression filter 30 shown in FIG. 4 and described above.

Difference signals $\Delta_n^1$, $\Delta_n^2$, $\Delta_n^3$, from the digital compression filters 30-1, 30-2, and 30-3, respectively, are switched, under control of a 3 to 1 digital multiplexer 500, to the encoder 40, which encoder may be of the same type as that shown in FIG. 5 and described above. The difference signals are sequentially encoded using the truncated Huffman type code depicted in FIG. 3. Whenever an else signal, 000001, is produced by the encoder 40, a signal is supplied to the timing and control unit 24A over line 28 indicating that the actual difference signal value $\Delta_n$ is required from the encoder, whereupon the encoder is controlled to provide the actual difference signal value $\Delta_n$ at the encoder output. In this case the encoder output comprises the actual difference signal value together with the code word for else as a label therefor. In FIG. 8A, a separate multiplexer control unit 502 is shown for addressing the multiplexer 500, which control unit simply may comprise a part of timing and control unit 24A. Encoded difference signal outputs from the encoder 40 are shown in FIG. 8A wherein the code word for $\Delta_n^i$ is designated $H(\Delta_n^i)$.

In order to distinguish signals from the three channels of information, a channel marker symbol, C, is periodically transmitted prior to the code word for $\Delta_n^1$. In FIG. 8A, the encoder output is supplied to line 504 through a switch 506, which switch is under control of an output from the multiplexer control unit 502. In the illustrated switch position, the encoded difference signals are passed through the switch to line 504. In the opposite switch position, the output from a channel marker unit 508 is supplied to the line 504. The channel marker unit 508, which also is under control of the multiplexer control unit 502, transmits a channel marker word, C, such as 000000001, periodically prior to the code word for $\Delta_n^1$. In the illustrated arrangement, the channel marker C is shown inserted every 32nd cycle of operation of the multiplexer 500. It will be seen that the illustrated channel marker word includes one more leading zero than the code word for $\Delta_n = -3$, and is readily decoded in the same manner as the other code words.

From line 504 the encoded ECG digital data is connected through switch 48 to buffer memory 50A and thence to digital modem 52A for transmission to a receiver, shown in FIG. 8B, over a conventional telephone transmission line 54. Alternatively, the signal may be recorded, when the switch 48 is in the opposite switch position, by recording means 60A. The buffer memory 50A, digital modem 52A, and recording unit 60A are of the same type shown in FIG. 1A and described above.

The receiver, shown in FIG. 8B, includes a digital modem 70, buffer memory 72, and switch 74 of the type shown in FIG. 1B and described above. A playback unit 100 also is included for playing back recorded ECG signals. From switch 74, the encoded digital signals are supplied to decoder 80A which is of the same general type as decoder 80 shown in FIG. 6, but which is modified to accommodate the channel marker, C. (For use with a channel marker, the ROM 302 included in the decoder would include storage of a symbol for the channel marker, which could be passed to the decoder output whenever the channel marker, C, is present at the decoder input. Also, counter 300 in the decoder would be required to count between 0-8, and an additional output line from the counter would be required to accommodate the additional place.)

As seen in FIG. 8B, the decoder output is supplied to a 1-3 digital demultiplexer 600 and to a channel marker detector 602 through a small buffer memory 84A. Demultiplexer outputs are connected to digital decompression filters 90-1, 90-2 and 90-3 which may be of the same type as shown in FIG. 7 and described above. Upon detection of a decoded channel marker, the channel marker detector 602 transmits a synchronizing signal to a multiplexer control unit 604 for resynchronizing the same. The decoded channel marker is prevented from entering the digital decompression filters 90-1, 90-2 and 90-3. Outputs from the digital decompression filters 90-1, 90-2 and 90-3 are supplied to digital to analog converters 96-1, 96-2 and 96-3, respectively, for conversion of the digitized signals to analog form. Any desired use may be made of the vector ECG from the digital to analog converters.

As noted above, equation (5) requires two successive values of $f_n$ as initial conditions. If some $\Delta_n$'s are lost after one or more bit errors, the reconstructed $f_n$ as calculated by equation (5) will differ from the true $f_n$ by a ramp of unknown slope. Where the system is not subject to bit errors, such as errors caused by transients in the transmission line, the use of such compression-decompression filter combination is acceptable. In a modified form of this invention a compression-decompression filter combination which is stable is employed, and one such stable combination now will be described.

The Z-transform of the double difference equation $\Delta_n = 0.5\ (f_{n+1} - 2f_n + f_{n-1})$, equation (3) above, is $$\frac{\Delta(Z)}{f(Z)} = 0.5\ (Z - 2 + Z^{-1}) \tag{6}$$

$$= 0.5Z(1 - 2Z^{-1} + Z^{-2})$$

$$= 0.5 \frac{(1 - Z^{-1})(1 - Z^{-1})}{Z^{-1}}$$

Consider the following modification of equation (6):

$$\frac{\Delta Z}{f(Z)} = 0.5 \frac{(1 - aZ^{-1})(1 - aZ^{-1})}{Z^{-1}} \tag{7}$$

$$= 0.5\ (Z - 2a + a^2Z^{-1})$$

The corresponding difference equation is:

$$\Delta_n = 0.5\ (f_{n+1} - 2af_n + a^2 f_{n-1}) \tag{8}$$
$$= 0.5 f_{n+1} - f_n + 2^{-m} f_n + 0.5 f_{n-1} - 2^{-m} f_{n-1} + 2^{-2m-1} f_{n-1}$$

where:
$a = 1 - 2^{-m}$ and
$m = $ an integer $> 0$

With proper timing and control, it will be apparent that the digital compression filter 30 shown in FIG. 4 and described above may be used to implement equation (8). With the apparatus shown in FIG. 4, equation (8) is implemented simply by shifting and adding operations, in a manner similar to the implementation of equation (3). From equation (8) it will be seen that sample signals are multiplied by $2^{-m-1}$ and $2^{-m}$; simply accomplished in the ALU by a shift of the indicated sample signals $-m-1$ and $-m$ spaces, respectively, toward the least significant bit position. The $f_{n+1}$, $f_n$ and $f_{n-1}$ signals simply are shifted the indicated number of spaces, and the indicated additions and subtractions are performed in the generation of the difference signal $\Delta_n$.

The inverse of equation (8) is:

$$\frac{f(Z)}{\Delta(Z)} = \frac{2Z^{-1}}{(1 - aZ^{-1})(1 - aZ^{-1})} \tag{9}$$

and the corresponding difference equations are:

$$y_n = 2\Delta_n + ay_{n-1} = 2\Delta_n + y_{n-1} - 2^{-m} y_{n-1} \tag{10}$$

$$f_n = y_n + af_{n-1} = y_n + f_{n-1} + 2^{-m} f_{n-1} \tag{11}$$

Since $$y_{n-1} = af_{n-2} - f_{n-1},$$

the starting equations are:

$$y_3 = 2\Delta_3 - af_2 + a^2 f_1 \tag{12}$$

$$f_3 = y_3 + af_2 \tag{13}$$

It may be shown that:

$$y_n = 2 \sum_{i=0}^{n-3} a^i \Delta_{n-i} + (a^n f_1 - a^{n-1} f_2) \tag{14}$$

$$f_n = \sum_{i=0}^{n-3} a^i y_{n-1} + a^{n-2} f_2 \tag{15}$$

When $a < 1$ the error due to incorrect values of $f_1$ and $f_2$ will die out faster than $a^n$. With a proper choce of m, this can be rapid. A value of m between, say, 2 to 6 is preferred.

There is no round-off error if the arithmetic word length is $2m+2$ bits longer than the input word length. Equations (14) and (15) make it clear why the prior art double integrator ($a=1$) adds a random ramp if incorrect values of $f_1$ and $f_2$ are supplied to the reconstruction filter. With both the prior art and present filter combinations, the output from the decompression filter 90 is identical to the input to the compression filter 30 when there are no transmission errors. Consequently, the transmission is without distortion under error-free transmission conditions. By making m large, the compression-decompression filter combination of the present invention may be made to function as close as desired to the double-difference, double integration scheme.

Figure 9:
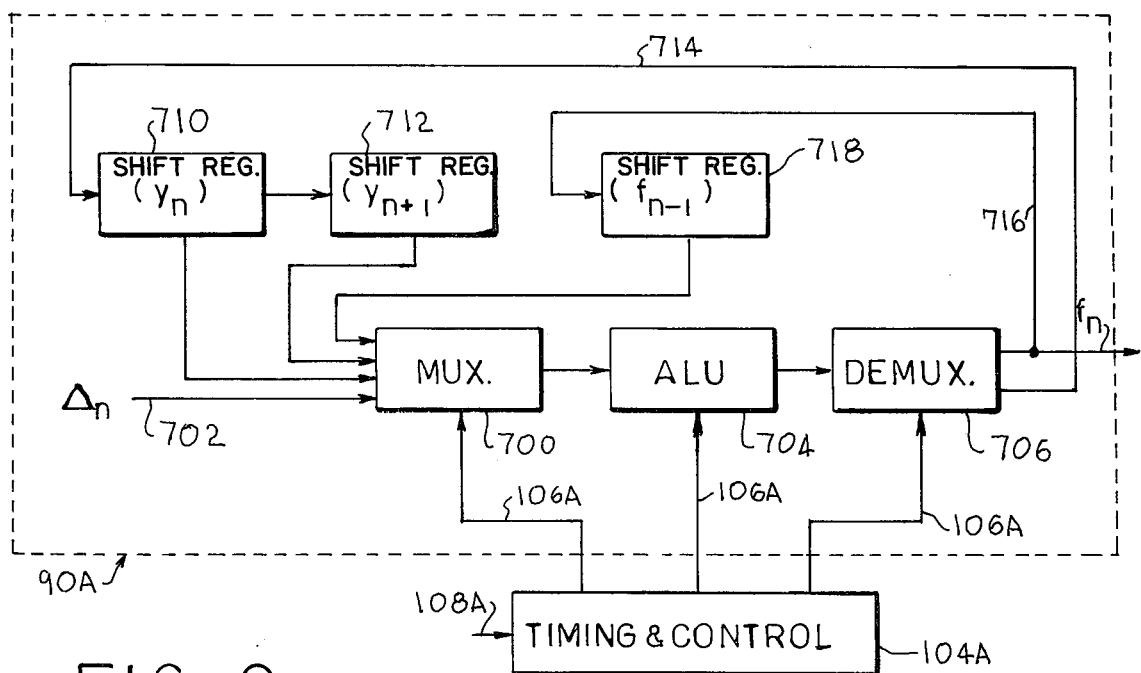
FIG. 9 is a block diagram showing details of a modified form of reconstruction filter embodying the present invention.

A novel digital reconstruction filter for implementing equations (10) and (11) is shown in FIG. 9, to which figure reference now is made. The illustrated reconstruction filter, identified by reference character 90A, comprises a 4 to 1 digital multiplexer 700 having one input 702 to which difference signals $\Delta_n$ are supplied from the decoder 80. (See E at FIG. 2) The output from the multiplexer 700 is supplied to an arithmetic and logic unit, ALU, 704 where the required multiplication by shifting, addition and subtraction take place, all under control of timing and control unit 104A.

The output from ALU 704 is connected to the input of a 1 to 2 digital demultiplexer 706. One output of demultiplexer 706 is connected to one register of a pair of series connected shift registers 710 and 712 over line 714. The other demultiplexer output is connected over line 716 to a single shift register 718. The value of $y_n$ determined by the ALU is loaded into register 710 while the prior value of $y_n$ is shifted from the register 710 into register 712. The third register 718 is supplied with the register value $f_n$ as calculated by ALU 704. Outputs from registers 710, 712 and 718 are supplied as inputs to the ALU 704 through the multiplexer 700. When used, the value stored in register 718 comprises $f_{n-1}$. From equation (10) it will be seen that the value $y_n$ is calculated using the $\Delta_n$ and $y_{n-1}$ inputs to ALU 704 available at line 702 and from register 710. From equation (11) it will be seen that the sample value $f_n$ is calculated using the $y_n$ and $f_{n-1}$ inputs from registers 710 and 718, respectively. As noted above, with this decoder there is no round-off error if the arithmetic word length is 2m+2 bits longer than the required input word length. For example, with a required input word length of 8, and with m=5, a word length of 8+2×5+2=20 wuld be used in the filter 90A. With the digital reconstruction filter 90A illustrated in FIG. 9 to implement equations (10) and (11), neither initialization nor reinitialization of the filter is required. Any transients essentially disappear after a relatively small number of samples following error bits.

The transfer function of the compression filter that is given in equation (7) contains two zeros on the real axis of the Z-plane, and the transfer function of the corresponding reconstruction filter contains two poles located at the same point on the real axis. Efficient compression can be obtained even when the zeros are not co-located; i.e., a double zero in the compression filter transfer function is not necessary. The zeros can be at different points on the real axis. There must be a pole in the reconstruction filter transfer function at points identical to the location of the zeros.

The difference equations for such a compression filter are:

$$y_n = 0.5 f_n - 0.5 f_{n-1} + 2^{-m_1} f_{n-1} \quad (16)$$

$$\Delta_n = y_n - y_{n-1} + 2^{-m_2} y_{n-1} \quad (17)$$

The difference equations for the reconstruction filter are:

$$y_n = 2\Delta_n + y_{n-1} - 2^{-m_1} y_{n-1} \quad (18)$$

$$f_n = y_n + f_{n-1} - 2^{-m_2} f_{n-1} \quad (19)$$

where $m_1$ and $m_2$ are positive integers.

The bandwidth of this latter reconstruction filter should be the same as the bandwidth of the filter whose transfer function is given in equation (9) for equivalent compression and recovery time.

Good efficiency also may be obtained with two complex zeros in the transfer function of the compression filter. The difference equation then is:

$$\Delta_n = f_n - 2 f_{n-1} + 2^{-m_1+1} f_{n-1} \\ + f_{n-2} - 2^{-m_1+1} f_{n-2} \\ 2^{-2m_1} f_{n-2} + 2^{-2m_2} f_{n-2} \quad (20)$$

The equation for the corresponding reconstruction filter is:

$$f_n = \Delta_n + 2 f_{n-1} - 2^{-m_1+1} f_{n-1} - f_{n-2} \\ + 2^{-m_1+1} f_{n-2} - 2^{-2m_1} f_{n-2} - 2^{-2m_2} f_{n-2} \quad (21)$$

where $m_1$ and $m_2$ again are positive integers.

It will be apparent that equations (16), (17) and (20) may be implemented using the compression filter 30 shown in FIG. 4, and that equations (18), (19) and (21) may be implemented using the reconstruction filter 90A shown in FIG. 9, each with proper timing and control to perform the indicated operations.

The invention having been described in detail in accordance with requirements of the Patent Statutes, various other changes and modifications will suggest themselves to those skilled in this art, which changes and modifications are intended to fall within the spirit and scope of the invention as defined in the appended claims.

I claim:

1. In a system for processing a plurality of simultaneously occuring analog signals, which system includes,
    a plurality of analog to digital converter means responsive to individual analog signals for converting the same to fixed length digital sample signals,
    a plurality of digital compression filter means individually responsive to outputs from said analog to digital converter means for generating a plurality of difference signals related to the difference between the sample signal input thereto and an estimated value thereof,
    digital encoder means, and
    digital signal multiplexer means for sequentially connecting said difference signals from said digital compression filter means to said digital encoder means for sequentially encoding said difference signals and providing a serial stream of digital encoded difference signals.

2. In a system as defined in claim 1 including
    means for connecting the serial stream from said digital encoder means to a telephone transmission line for transmission thereof to remove receiving means.

3. In a system as defined in claim 2 including remote receiving means comprising,
    decoding means for decoding the serial stream received from said digital encoder means over the telephone transmission line
    digital signal demultiplexing means responsive to the decoded serial stream from the decoding means to provide a plurality of difference signal streams, and
    a plurality of digital decompression filter means individually responsive to the difference signal streams from said demultiplexing means for conversion of said difference signals to fixed length sample signals.

4. In a system as defined in claim 3 wherein said plurality of digital compression filter means and said plurality of digital decompression filter means comprise a plurality of stable compression-decompression filter combinations in which transients disappear following error bits in transmission of the serial stream from said digital encoder means to said remote receiving means.

5. In a system as defined in claim 1 wherein said plurality of simultaneously occuring analog signals comprise ECG signals.

6. In a system as defined in claim 5 wherein said ECG signals comprise a vector ECG.

7. In a system as defined in claim 1 wherein said digital encoder means comprises a Huffman encoder for implementing a truncated-type Huffman code.

8. In a system as defined in claim 1 wherein each of said digital compression filter means has a transfer function $$\Delta_n = y_n - y_{n-1} +$$

$$2^{-m_2}y_{n-1}$$

wherein:

$$y_n = 0.5f_n - 0.5f_{n-1} + 2^{-m_1-1}f_{n-1},$$

$f_n$ is the input to the digital compression filter means, $\Delta_n$ is the difference signal output from the digital compression filter means, and $m_1$ and $m_2$ are positive integers.

9. In a system as defined in claim 8 wherein each of said digital compression filter means comprises an arithmetic and logic unit.

10. In a system as defined in claim 1 wherein each of said digital compression filter means has a transfer function $$\Delta_n = f_n - 2f_{n-1} + 2^{-m_1+1}f_{n-1} + f_{n-2} - 2^{-m_1+1}f_{n-2} + 2^{-2m_1}f_{n-2} + 2^{-2m_2}f_{n-2}$$

wherein:

$f_n$ is the input to the digital compression filter means, $\Delta_n$ is the difference signal output from the digital compression filter means, and $m_1$ and $m_2$ are positive integers.

11. In a system as defined in claim 1 including means for recording the serial stream from said digital encoder means.

12. In a system as defined in claim 11 including means for playback of the recorded serial stream.

13. In a system as defined in claim 12 wherein said playback means has a serial stream output corresponding to the recorded serial stream from said digital encoder means, said system including, decoding means for decoding the serial stream output from said playback means, digital signal demultiplexing means responsive to the decoded serial stream from the decoding means to provide a plurality of difference signal streams, and a plurality of digital decompression filter means individually responsive to the difference signal streams from said demultiplexing means for conversion of said difference signals to fixed length sample signals.

14. In a system as defined in claim 13 wherein said plurality of digital compression filter means and said plurality of digital decompression filter means comprise a plurality of stable compression-decompression filter combinations in which transients disappear following error bits in the serial stream output from said playback means.

15. In a system as defined in claim 14 wherein said plurality of simultaneously occuring analog signals comprise ECG signals.

16. In a system as defined in claim 15 wherein said ECG signals comprise a vector ECG.

17. In a system as defined in claim 14 wherein said digital encoder means comprises a Huffman encoder for implementing a truncated-type Huffman code.

18. In a system as defined in claim 14 wherein each of said digital compression filter means has transfer function $$\Delta_n = y_n - y_{n-1} + 2^{-m_2}y_{n-1}$$

wherein:

$$y_n = 0.5f_n - 0.5f_{n-1} + 2^{-m_1-1}f_{n-1},$$

$f_n$ is the input to the digital compression filter means, $\Delta_n$ is the difference signal output from the digital compression filter means, and $m_1$ and $m_2$ are positive integers.

19. In a system as defined in claim 18 wherein each of said digital compression filter means comprises an arithmetic and logic unit.

20. In a system as defined in claim 14 wherein each of said digital compression filter means has a transfer function $$\Delta_n = f_n - 2f_{n-1} + 2^{-m_1+1}f_{n-1} + f_{n-2} - 2^{-m_1+1}f_{n-2} + 2^{-2m_1}f_{n-2} + 2^{-2m_2}f_{n-2}$$

wherein:

$f_n$ is the input to the digital compression filter means, $\Delta_n$ is the difference signal output from the digital compression filter means, and $m_1$ and $m_2$ are positive integers.

21. In a system for processing a plurality of streams of digital sample signals obtained from analog to digital converters, or the like, comprising a plurality of digital compression filter means responsive to individual digital sample signal streams for compression encoding said digital sample streams, digital encoder means, and means for sequentially connecting outputs from said plurality of digital compression filter means to said digital encoder means for sequential encoding by said digital encoder means of outputs from said plurality of digital compression filter means.

22. In a system as defined in claim 21 including, means for connecting the output from the digital encoder means to a telephone transmission line for transmission to a remote receiving means.

23. In a system as defined in claim 21 including, means for recording the output from the digital encoder means.

24. In a system which includes a plurality of streams of digital sample signals, the method of processing said digital sample signal streams comprising, for each digital sample signal stream, generating a corresponding stream of difference signals related to the difference between digital sample signals and an estimated value thereof whereby a separate stream of difference signals is generated for each stream of digital sample signals, interspersing said difference signal streams to provide a serial stream of difference signals, and digitally encoding said serial stream of difference signals.

25. The method as defined in claim 24 including transmitting the digitally encoded serial stream of difference signals over a telephone transmission line to a remote receiver.

26. The method as defined in claim 24 including recording the digitally encoded serial stream of difference signals.

* * * * *